United States Patent [19]

Foster et al.

[11] 4,377,712

[45] Mar. 22, 1983

[54] PREPARATION OF META-SUBSTITUTED DIARYL ETHERS

[75] Inventors: Arthur M. Foster, Birmingham, Mich.; James J. Maul, Grand Island, N.Y.

[73] Assignee: Occidental Chemical Corporation, Niagara Falls, N.Y.

[21] Appl. No.: 237,194

[22] Filed: Feb. 23, 1981

Related U.S. Application Data

[63] Continuation-in-part of Ser. No. 28,297, Apr. 9, 1979, abandoned.

[51] Int. Cl.$^3$ ............................................. C07C 41/16
[52] U.S. Cl. .................................. 568/635; 568/585; 568/586; 568/636; 568/637; 549/201
[58] Field of Search ............... 568/585, 586, 635, 636, 568/627, 637; 549/201

[56] References Cited

U.S. PATENT DOCUMENTS

3,567,781  3/1971  Clark .................................. 568/636
4,112,002  9/1978  Schneider et al. .................. 568/585

FOREIGN PATENT DOCUMENTS

222360  10/1968  U.S.S.R. ............................. 568/635

*Primary Examiner*—Bernard Helfin
*Attorney, Agent, or Firm*—James F. Tao; A. S. Cookfair; W. G. Gosz

[57] ABSTRACT

A process for the preparation of meta-substituted diaryl ethers comprises reacting an ortho-haloaryl compound with a phenol compound in a non-aqueous medium in the presence of an alkaline metal base. In a specific embodiment m-phenoxytoluene is prepared by reacting orthochlorotoluene with phenol in the presence of an alkaline metal hydroxide in a substantially non-aqueous liquid medium.

23 Claims, No Drawings

PREPARATION OF META-SUBSTITUTED DIARYL ETHERS

This is a continuation-in-part of Ser. No. 028,297 filed Apr. 9, 1979 and now abandoned.

BACKGROUND OF THE INVENTION

This invention relates to an improved process for the preparation of meta-substituted diaryl ethers especially m-phenoxytoluenes. The compounds prepared are known in the art to be useful in a variety of commercial applications, as heat transfer agents, and as intermediates in the preparation of synthetic pyrethroid pesticides.

Various processes for the preparation of diaryl ethers, have been reported in the literature. In general, the processes of the prior art can be described in terms of two classes of process. In one class of prior art processes, the product obtained from two aryl reactants is primarily a single diaryl-ether compound produced by nucleophilic substitution of a phenol (phenolate) compound for a halogen on the nucleus of the second aryl reactant, at the site of the halogen atom. In the second class of processes, the diarylether product is an isomeric mixture, at least partially derived from a single starting material. The process typically involves the formation of a nucleophile by hydrolysis of an aryl reactant followed by reaction of the nucleophile with a second molecule of the aryl reactant.

U.S. Pat. No. 1,099,761 discloses the preparation of aryl ethers by the reaction of an aromatic halogenated hydrocarbon with a dry alkali phenolate dissolved in phenol with heat and pressure. In this manner the patent specifically teaches the preparation of m-cresylphenyl ether (M-phenoxytoluene) by reaction of chlorobenzene with dry m-potassium cresylate dissolved in m-cresol.

U.S. Pat. No. 3,032,594 discloses the preparation of dinitrodiphenyl ether by reaction of an alkali metal salt of nitrophenol with chloronitrobenzene in dimethyl sulfoxide solvent.

U.S. Pat. No. 3,634,519 teaches a process for the production of diarylethers by reaction of a p-halo-nitro aromatic compound with an aqueous solution of an alkali metal hydroxide in a polar organic solvent such as dimethyl sulfoxide.

U.S. Pat. No. 3,755,467 discloses the preparation of halogen-containing aryl ethers by a process which comprises the reaction of an alkali metal phenolate with a trihalobenzene in the presence of a strongly polar organic solvent, such as dimethyl sulfoxide, at an elevated temperature.

Japanese Pat. No. 74/62432 discloses the preparation of m-phenoxytoluene by reaction of an alkali metal salt of m-cresol with chlorobenzene in the presence of an organic base and a catalytic amount of copper or copper compound.

U.S. Pat. No. 4,092,364 discloses a process for the preparation of diphenyl oxide by caustic hydrolysis of chlorobenzene and recycling of by-product phenol to maximize the yield of diphenyl oxide as well as the yield of phenylphenol and biphenylphenyl ether by-products.

In British Pat. No. 1,191,409 it is disclosed that ditolyl ether mixtures may be prepared in an industrial scale by the reaction of chloroetoluenes alone or mixtures of chlorotoluenes and cresols in the presence of an aqueous sodium hydroxide solution at temperatures of 250° to 400° C. and under pressures of 100 to 300 atmospheres. The process disclosed is non-selective and thus produces a mixture of ditolyl ethers.

Although various processes for the preparation of diaryl ethers are known in the prior art, it will be appreciated that still further improvements are desirable, such as improvements in product selectivity and purity, the use of more economical reactant, and less stringent reaction conditions, such as lower reaction pressures.

It is an object of the present invention to provide an improved process for the preparation of meta-substituted diaryl ethers. It is a further object to provide an improved method for the preparation of meta-substituted diaryl ethers wherein the aryl groups differ from each other. It is a still further object to provide an improved method for the preparation of meta-substituted diaryl-ethers wherein at least one of the starting materials is a readily available ortho-haloaryl isomer. It is a more specific object to provide an improved method for the preparation of m-phenoxytoluene. It is a still further object to provide such a process for the preparation of m-phenoxytoluene from readily available and economically attractive reactants, such as phenol and ortho-chlorotoluene.

SUMMARY OF THE INVENTION

It has now been found that meta-substituted diarylethers of the general formula

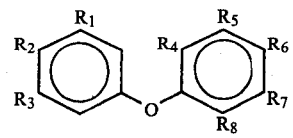

(Ar$_1$)   (Ar$_2$)

wherein $R_1$ is selected from the group consisting of alkyl and alkoxy of 1 to 30 carbon atoms, aryl and aryloxy of 6 to 14 carbon atoms and 2-(1,3)dioxolyl; $R_2$ and $R_3$ are independently selected from the group consisting of hydrogen, alkyl and alkoxy of 1 to 30 carbon atoms, aryl and aryloxy of 6 to 14 carbon atoms; $R_5$, $R_6$, and $R_7$ are independently selected from the group consisting of hydrogen, nitro, alkyl and alkoxy of 1 to 30 carbon atoms, aryl and aryloxy of 6 to 14 carbon atoms; $R_4$ and $R_8$ are independently selected from the group consisting of hydrogen, nitro, and linear alkyl and alkoxy of 1 to 4 carbon atoms, with the proviso that if either $R_4$ or $R_8$ is a substituent of more than 2 carbon atoms the other substituent is hydrogen may be prepared by the reaction of an ortho-halo aryl compound (Ar$_1$) of the formula

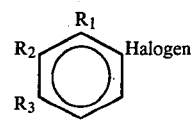

wherein $R_1$ through $R_3$ are as previously defined and halogen is bromine or chlorine, with a phenol compound (Ar$_2$) of the formula

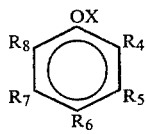

wherein R<sub>4</sub> through R<sub>8</sub> are as previously defined and X is hydrogen or an alkali metal, in a substantially non-aqueous medium in the presence of an excess of base.

Although it is not intended to be bound by any particular theory as to the reaction mechanism of the process of the present invention, it is postulated that the reaction proceeds with the formation of a benzyne intermediate generated from the orthohaloaryl reactant which then permits phenoxide substitution at the ortho and meta positions. Substitution at the meta position usually predominates, partially because of the steric requirements of $R_1$, and of the phenol moiety ($Ar_2$).

The alkyl, alkoxy, aryl, and aryloxy substituents which may be present at the designated $R_1$ through $R_8$ positions of the $Ar_1$ and $Ar_2$ reactants may vary considerably and may be substituted or unsubstituted. Suitable aryl or aryloxy or substituted aryl or aryloxy substituents include those of 6 to 14 nuclear carbon atoms, such as phenyl, phenoxy, naphthyl, naphthoxy, anthryl, and the like and preferably 6 carbon atoms. Suitable alkyl or alkoxy substituents or substituted alkyl or alkoxy substituents include branched or straight chain alkyl or alkoxy groups of 1 to 30 carbon atoms, and preferably lower alkyl or alkoxy of 1 to 4 carbon atoms, and most preferably methyl or methoxy. The substituted alkyl or alkoxy groups include haloalkyl and haloalkoxy, such as trifluoromethyl, and trifluoromethoxy.

Suitable $Ar_1$ reactants include, for example ortho-halo compounds such as o-chlorotoluene, o-bromotoluene, o-chloroethylbenzene, o-bromo-ethylbenzene, o-chloro-propylbenzene, o-bromo-propylbenzene, o-chloro-butylbenzene, o-bromo-butylbenzene, and the like. A preferred $Ar_1$ reactant is ortho-chlorotoluene.

Suitable $Ar_2$ reactants include, for example, phenol, the alkyl phenols, such as ortho, meta, and para cresol, ethyl phenol, propylphenol, butylphenol, and the like, dialkylphenols such as dimethyl, diethyl, dipropyl and dibutyl phenols, carvacrol, and the like, alkoxy phenols such as guaiacol, and the like and nitro phenols such as ortho, meta and para nitrophenol, dinitrophenols, nitrodicresols, dinitrocresol, dinitrocyclohexylphenol, dinitrobutylphenol and the like as well as the corresponding alkali metal phenolates. Preferred $Ar_2$ reactants are phenol or an alkali metal phenoxide, especially sodium or potassium phenoxide.

In the process, the ortho-haloaryl compound and phenol compound are reacted in the presence of an excess of base, that is, an amount of base in excess of that required to convert the phenol present to the phenoxide. The base employed in the reaction should be a strong enough base to generate a benzyne intermediate but of low enough nucleophilicity to avoid excessive competition with the phenoxide present. Preferred bases are alkali metal hydroxides or carbonates such as KOH or $Na_2CO_3$, or mixtures thereof. The molar ratio of base to phenol compound is greater than one and preferably in the range of about 1 to about 4 based on phenol, or greater than 0 to about 3, based on alkali metal phenoxides. Larger excesses of base may be employed, but will generally result in an increase of undesired by-products, such as ditolyl ethers, and thus are not preferred.

In the process of this invention the reaction of the ortho-haloaryl compound and the phenol may be carried out at atmospheric pressure and at temperatures up to about the reflux temperature of the reaction medium. Under such conditions the reaction is carried out in the presence of a suitable non-aqueous solvent. Preferred solvents for this purpose include aprotic, substantially non-nucleophilic polar solvents, such as dimethyl sulfoxide, diethyl sulfoxide, dimethyl-sulphone, diethyl-sulphone, diisopropyl-sulphone, tetramethyl-sulphone, quinoline, pyridine and the like. Higher temperatures may be employed, preferably in the absence of a solvent, for example, by contacting the ortho-haloaryl reactant in a fluidized bed of the phenoxide and base. Alternatively, utilizing autoclave techniques, the reaction may be carried out at temperatures above the reflux temperature, for example, up to about 400° C. or higher, at autogenous pressures. When the reaction is carried out at elevated temperatures and pressures, a suitable inert solvent, preferably one that is not susceptible to decomposition under reaction conditions, such as benzene, toluene, or the like, may be employed. However, under such conditions it is preferred to carry out the process in the absence of a solvent.

It is a particular advantage of the present invention that the generally less expensive ortho-haloaryl compounds, especially ortho-chlorotoluene, may be employed as a starting material to effect an oxide substitution at the meta position.

The following specific examples are provided to further illustrate this invention in a manner in which it may be carried out. It will be understood however, that the specific details given in the Examples have been chosen for purposes of illustration and are not be construed as a limitation on the invention. In the Examples, unless otherwise indicated all parts and percentages are by weight and all temperatures are in degrees celsius.

EXAMPLE I

A mixture of 22.4 parts of reagent grade (85%) potassium hydroxide, 16.0 parts of sodium hydroxide, and 18.8 parts of phenol in 55 parts of quinoline was heated to 100° C., with stirring. The reaction mixture was then allowed to cool to approximately room temperature and 30.4 parts of 2,-chlorotoluene was added, with stirring. The reaction mixture was then heated, with agitation, and maintained at about reflux temperatures (170°–178° C.) for a period of about eleven hours, during which time water was azeotroped out of the reaction mixture. The reaction mixture was then allowed to cool. Water was added, and the organic material extracted with toluene, washed and dried. The dried extract was analyzed by gas chromatographic techniques and found to contain a 20% yield of ortho and meta-phenoxy toluene, in a ratio of meta/ortho of 2.53.

EXAMPLE II

A mixture of 44.4 parts of 85% potassium hydroxide and 18.8 parts of phenol in about 50 parts of dimethyl sulfoxide was heated to 100° C. with stirring. The reaction mixture was allowed to cool and 30.4 parts of 2,-chlorotoluene was added. The reaction mixture was heated, with stirring, to reflux temperature (approximately 160° C.) and maintained thereat for about 20 hours. The reaction mixture was then cooled and 100 parts of water was added resulting in a phase separation of an aqueous layer and an organic layer. The organic layer was washed with two additional portions of water (50 parts) to yield 31.0 parts of organic liquid. Analysis of the organic product by gas chromatographic techniques indicated a 44% conversion to ortho and meta phenoxy toluene, in a meta/ortho ratio of 1.64.

EXAMPLE III

A mixture of 18.8 parts of phenol, 32.0 parts of sodium hydroxide, and 108 parts of toluene was heated to reflux and toluene and the water of condensation, resulting from the formation of sodium phenoxide, was continuously removed in vapor form. The mixture was then heated to about 330° C. and the toluene removed by distillation. Then 12.4 parts of o-chlorotoluene was added over a period of about 3.75 hours, while the reaction mixture was maintained at about 260°–330° C. Following the addition of the o-chlorotoluene, the reaction mixture was maintained at about 260°–330° C. for an additional 4.75 hours. The reaction mixture was then cooled, water was added, and the organic material was extracted with toluene. Analysis of the organic product by gas chromatographic techniques indicated a yield of 7.6% based on o-chlorotoluene, of ortho- and meta-phenoxytoluene, in a meta/ortho ratio of 1.86.

EXAMPLE IV

Sodium amide was prepared by dissolving 9.3 parts of sodium metal in a stirred solution of 0.05 parts of ferric nitrate and 300 parts of liquid ammonia at reflux conditions and maintained under a positive pressure of nitrogen. The resultant sodium amide solution was stirred while 14.1 parts of phenol was added over a 20 minute period then 6.3 parts of o-chlorotoluene was added over a 15 minute period. After stirring an additional 60 minute, 17.4 parts of ammonium chloride was added portion-wise over a period of 20 minutes. The ammonia was allowed to evaporate overnite. Water (150 parts) was added and the organic product was extracted with ether. After washing and drying, the ether extract was concentrated. The residue was analyzed bia gas chromatographic techniques which indicated a 1.0% conversion to ortho- and meta-phenoxytoluene in a meta/ortho ratio of 2.41.

EXAMPLE V

A mixture of 28.2 parts of phenol, 19.5 parts of 85% potassium hydroxide and 300 parts of toluene was heated at reflux and then distilled to dryness under $N_2$ to remove all water present. An additional 9.8 parts of 85% potassium hydroxide (9.8 parts) and 113.4 parts of 2-chlorotoluene were added and the mixture was stirred in an autoclave at 350° C. for 4 hours. The mixture was cooled, water was added and the organic product was extracted with ethyl-ether. After filtration, the ether layer was separated and analyzed by gas chromatographic techniques which indicated an 80% conversion to ortho- and meta-phenoxytoluene with a meta/ortho ratio of 1.86.

EXAMPLE VI

A mixture of 11.8 parts of sodium phenoxide, 4.0 parts of sodium hydroxide, and 38.1 parts of 2-chlorotoluene was stirred in an autoclave at 350° C. for 4 hours. After cooling, 50 parts of $H_2O$ was added and the organic material was extracted with ethyl-ether. Evaporation of the ether solvent yielded 38.7 parts of organic liquid. Analysis of the organic product by gas chromatographic techniques indicated a 45.2% conversion to ortho- and meta-phenoxytoluene, in a meta/ortho ratio of 2.14.

EXAMPLE VII

A mixture of 44.8 parts of 85% potassium hydroxide, 18.8 parts of phenol, and 55 parts of quinoline were stirred and heated at 150° C. for 2.5 hours; 2-chlorotoluene (3014 parts) was added and the mixture was then stirred in an autoclave at 350° C. for 2 hours. The reaction was cooled, water was added and the organic product was extracted with methylene chloride. The washed organic extract was concentrated and analyzed by gas chromatographic techniques which indicated a 13.9% yield of ortho- and meta-phenoxytoluene in a meta/ortho ratio of 0.64.

What is claimed is:

1. A process for the preparation of meta-substituted diaryl ethers of the formula

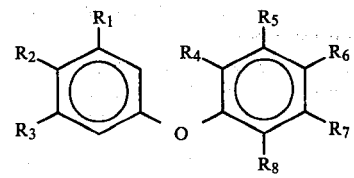

wherein $R_1$ is selected from the group consisting of alkyl and alkoxy of 1 to 30 carbon atoms, aryl and aryloxy of 6 to 14 carbon atoms and 2-(1,3)dioxolyl; $R_2$ and $R_3$ are independently selected from the group consisting of hydrogen, alkyl and alkoxy of 1 to 30 carbon atoms, aryl and aryloxy of 6 to 14 carbon atoms; $R_5$, $R_6$, and $R_7$ are independently selected from the group consisting of hydrogen nitro, alkyl and alkoxy of 1 to 30 carbon atoms, aryl and aryloxy of 6 to 14 carbon atoms; $R_4$ and $R_8$ are independently selected from the group consisting of hydrogen, nitro, and linear alkyl and alkoxy of 1 to 14 carbon atoms, with the proviso that if either $R_4$ or $R_8$ is a substituent of more than 2 carbon atoms the other substituent is hydrogen; comprising reacting at atmospheric pressure an ortho-halo aryl compound of the formula

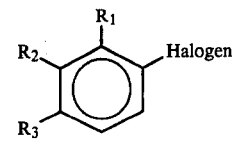

wherein $R_1$, $R_2$ and $R_3$ are as previously defined, and halogen is chlorine or bromine; with a phenol compound of the formula

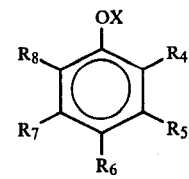

wherein $R_4$, $R_5$, $R_6$, $R_7$ and $R_8$ are as previously defined, and X is hydrogen or an alkali metal; in an aprotic, substantially non-nucleophilic, polar solvent at a temperature of about 110° Celsius to about the reflux temperature of the reaction medium, in the presence of an alkali metal base selected from an alkali metal hydroxide and alkali metal carbonate in a molar ratio of alkali metal base: phenol compound of greater than about 1.0 to about 4.0 when X is hydrogen and greater than about 0 to about 3.0 when X is an alkali metal.

2. A process according to claim 1 wherein the base is an alkali metal hydroxide.

3. A process according to claim 1 wherein the halogen of the ortho-haloaryl compound is chlorine.

4. A process according to claim 3 wherein the ortho-haloaryl compound is orthochlorotoluene.

5. A process according to claim 4 wherein the phenol compound is phenol.

6. A process according to claim 4 wherein the phenol compound is an alkali metal phenoxide.

7. A process according to claim 1 wherein the alkali metal base is sodium hydroxide.

8. A process according to claim 1 wherein the alkali metal base is potassium hydroxide.

9. A process according to claim 1 wherein the solvent is selected from the group consisting of dimethyl sulfoxide, diethyl sulfoxide, dimethyl sulfone, diethyl sulfone, diisopropylsulfone, tetramethylsulfone, quinoline and pyridine.

10. A process according to claim 6 wherein the molar ratio of alkali metal hydroxide:phenoxide is in the range of greater than 0 to about 3.0.

11. A process according to claim 10 wherein the alkali metal phenoxide is sodium phenoxide and the alkali metal hydroxide is sodium hydroxide.

12. A process according to claim 10 wherein the alkali metal phenoxide is potassium phenoxide and the alkali metal hydroxide is potasssium hydroxide.

13. A process according to claim 10 wherein the solvent is selected from the group consisting of dimethyl sulfoxide, diethyl sulfoxide, dimethyl sulfone, diethyl sulfone, diisopropysulfone, tetramethylsulfone, quinoline and pyridine.

14. A process for the preparation of meta-substituted diaryl ethers of the formula

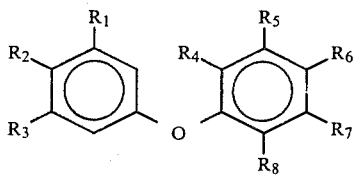

wherein R$_1$ is selected from the group consisting of alkyl and alkoxy of 1 to 30 carbon atoms, aryl and aryloxy of 6 to 14 carbon atoms and 2-(1,3)dioxolyl; R$_2$ and R$_3$ are independently selected from the group consisting of hydrogen, alkyl and alkoxy of 1 to 30 carbon atoms, aryl and aryloxy of 6 to 14 carbon atoms; R$_5$, R$_6$, and R$_7$ are independently selected from the group consisting of hydrogen, nitro, alkyl and alkoxy of 1 to 30 carbon atoms, aryl and aryloxy of 6 to 14 carbon atoms; R$_4$ and R$_8$ are independently selected from the group consisting of hydrogen, nitro, and linear alkyl and alkoxy of 1 to 14 carbon atoms, with the proviso that if either R$_4$ or R$_8$ is a substituent of more than 2 carbon atoms the other substituent is hydrogen; comprising reacting at autogenous pressure an ortho-halo aryl compound of the formula

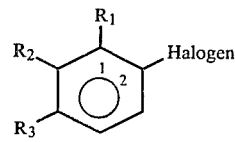

wherein R$_1$, R$_2$ and R$_3$ are as previously defined, and halogen is chlorine or bromine; with a phenol compound of the formula

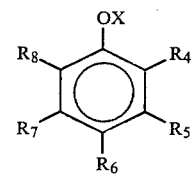

wherein R$_4$, R$_5$, R$_6$, R$_7$ and R$_8$ are as previously defined, and X is hydrogen or an alkali metal; at a temperature of from about reflux temperature to about 400° Celsius, in the presence of an alkali metal base selected from an alkali metal hydroxide and an alkali metal carbonate in a molar ratio of alkali metal base: phenol compound of greater than about 1.0 to about 4.0 when X is hydrogen and greater than about 0 to about 3.0 when X is an alkali metal.

15. A process according to claim 14 wherein the base is an alkali metal hydroxide.

16. A process according to claim 15 wherein the halogen of the ortho-haloaryl compound is chlorine.

17. A process according to claim 16 wherein the ortho-haloaryl compound is orthochlorotoluene.

18. A process according to claim 17 wherein the phenol compound is phenol.

19. A process according to claim 17 wherein the phenol compound is an alkali metal phenoxide.

20. A process according to claim 15 wherein the alkali metal hydroxide is potassium hydroxide.

21. A process according to claim 19 wherein the molar ratio of alkali metal hydroxide:phenoxide is in the range of greater than 0 to about 3.0.

22. A process according to claim 21 wherein the alkali metal phenoxide is sodium phenoxide and the alkali metal hydroxide is sodium hydroxide.

23. A process according to claim 21 wherein the alkali metal phenoxide is potassium phenoxide and the alkali metal hydroxide is potassium hydroxide.

* * * * *